United States Patent
Long et al.

(10) Patent No.: US 7,860,215 B2
(45) Date of Patent: Dec. 28, 2010

(54) IMAGING SYSTEMS FOR IONISING RADIATION

(75) Inventors: Andrew Long, Leatherhead (GB); Kevin Brown, Horsham (GB); John Allen, Haywards Heath (GB)

(73) Assignee: Elekta AB (publ), Stockholm (SE)

( * ) Notice: Subject to any disclaimer, the term of this patent is extended or adjusted under 35 U.S.C. 154(b) by 36 days.

(21) Appl. No.: 12/441,005

(22) PCT Filed: Sep. 13, 2006

(86) PCT No.: PCT/EP2006/008905

§ 371 (c)(1),
(2), (4) Date: Mar. 12, 2009

(87) PCT Pub. No.: WO2008/031443

PCT Pub. Date: Mar. 20, 2008

(65) Prior Publication Data

US 2010/0002836 A1    Jan. 7, 2010

(51) Int. Cl.
*A61N 5/10* (2006.01)
(52) U.S. Cl. .......................................... 378/65; 378/97
(58) Field of Classification Search .............. 378/64–65
See application file for complete search history.

(56) References Cited

U.S. PATENT DOCUMENTS 4,365,341 A * 12/1982 Lam ............................ 378/65

2004/0120452 A1   6/2004 Shapiro et al.
2005/0058237 A1 * 3/2005 Morf .............................. 378/4

FOREIGN PATENT DOCUMENTS

EP    1642528 A    4/2006
WO    9314418 A    7/1993

OTHER PUBLICATIONS

PCT International Search Report, Dec. 8, 2006.

* cited by examiner

*Primary Examiner*—Hoon Song
(74) *Attorney, Agent, or Firm*—Z. Peter Sawicki; Westman, Champlin & Kelly, P.A.

(57) ABSTRACT

Flat panel images obtained during concurrent radiotherapy typically suffer from artefacts that relate to the pulses of MV energy. For a radiotherapeutic apparatus comprising a pulsed source of therapeutic radiation, a detector comprising control circuitry, an array of pixel elements, each having a signal output and an 'enable' input and being arranged to release a signal via the signal output upon being triggered by the enable input, and an interpreter arranged to receive the signal outputs of the pixel elements, the interpreter having a reset control, there are advantages in the control circuitry being adapted to reset the interpreter after a pulse of therapeutic radiation, prior to enabling at least one pixel of the array. Alternatively, the control circuitry can prompt a plurality of pulses by the pulsed source and then enable a plurality of pixels of the array. In effect, the therapeutic pulses are grouped into a short flurry of pulses. It is therefore preferred that the plurality of pixels comprises substantially all the pixels of the array.

20 Claims, 3 Drawing Sheets

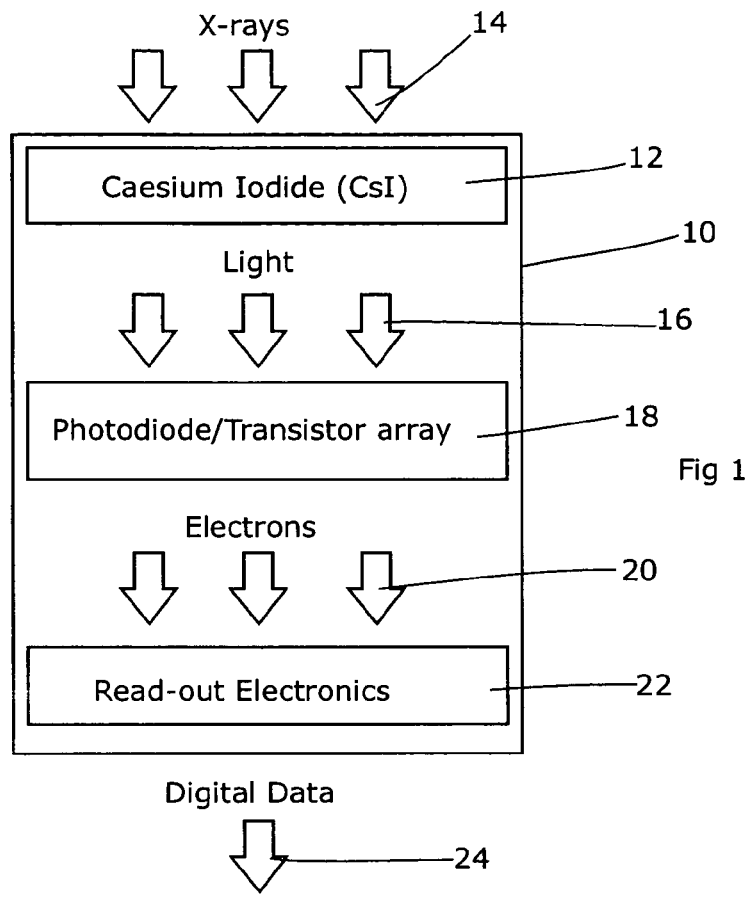
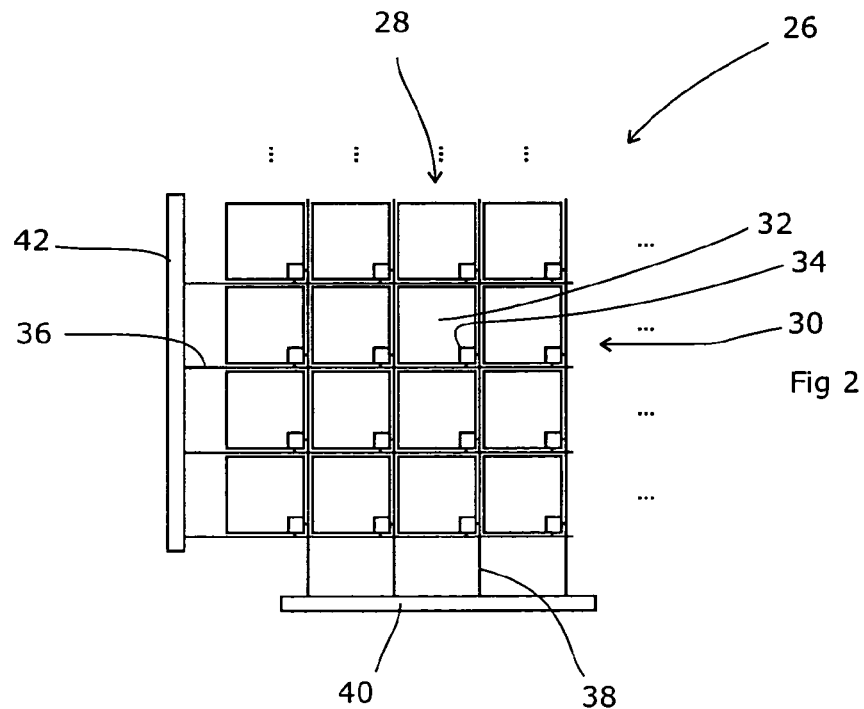
Fig 1
Fig 2 ically cools, and the device will warm up. However, this will be followed by a longer period in which the pulse rate is zero or reduced, allowing the device to cool. Provided the warm/cool cycle is shorter than the thermal time constant of the device, the average temperature of the device will not rise above design limits.

IMAGING SYSTEMS FOR IONISING RADIATION

CROSS-REFERENCE TO RELATED APPLICATION

This Application is a Section 371 National Stage Application of International Application No. PCT/EP2006/008905, filed Sep. 13, 2006 and published as WO 2008/031443 A1 on Mar. 20, 2008, the content of which is hereby incorporated by reference in its entirety.

FIELD OF THE INVENTION

The present invention relates to imaging systems for detecting ionising radiation.

BACKGROUND ART

Flat panel images are often used in radiotherapy and other applications in order to derive an image from ionising radiation that has (for example) passed through a patient. Diagnostic images are generally obtained from the use of kilovoltage (kV) radiation and can be used either as two dimensional images or can be used as one of a number of such two dimensional images in order to create three dimensional representations via computed tomography (CT). Therapeutic radiation tends to be in the megavoltage (MV) range and can also be used to derive a portal image. This is an image of the therapeutic radiation after it has passed through the patient; generally the image is of a low quality with poor contrast. Anatomical features are however apparent in the image and can be used to check (for example) that the patient is correctly positioned.

MV radiation produces an image with inherently low contrast and therefore it is important that no artefacts are present in the image to obscure the anatomy. The MV source typically operates in a pulsed manner at a duty cycle of approximately 1 in 1000 and therefore there is ample opportunity between pulses to obtain data from a few rows of the flat panel imager.

FIG. 1 shows the typical structure of a flat panel imager 10. An upper layer 12 consists of a scintillator under the application of x-rays 14. The light 16 thus produced impinges on an array 18 of photodiodes and transistors which are disposed in a layer immediately beneath the upper layer 12. The array 18 is divided into individual pixels, each of which is associated with a single photodiode. The light impinges on the photodiode in the array and creates an electronic signal which is gated appropriately by the transistor. The electronic signal 20 thus produced is extracted from the flat panel array via read-out electronics 22 to form a digital data stream 24 that is used to construct the image.

SUMMARY OF THE INVENTION

We have found that such portal images suffer from artefacts that relate to the pulses of MV energy. When a MV pulse arrives, it will not only cause scintillation in the scintillator, but will also impinge on the transistor array and the read-out electronics and ionise the material of which they are formed. This will therefore create a further electronic signal, entirely bypassing the scintillator and the photodiodes. We propose two ways in which these problems can be overcome.

In a first aspect, therefore, we provide a radiotherapeutic apparatus comprising a pulsed source of therapeutic radiation and a flat panel detector, the detector comprising control circuitry, an array of pixel elements, each having a signal output and an 'enable' input and being arranged to release a signal via the signal output upon being triggered by the enable input, and an interpreter arranged to receive the signal outputs of the pixel elements, the interpreter having a reset control, the control circuitry being adapted to reset the interpreter after a pulse of therapeutic radiation, prior to enabling at least one pixel of the array.

Thus, the interpreter reset remains on during (or is activated after) a therapeutic pulse. This then causes the system to ignore the charge collected as a result of the pulse and removes artefacts resulting therefrom.

Generally, the pixel elements of such detectors work by outputting a signal in which the total charge passed reflects the total incident radiation since the last time the pixel was read. As radiation is incident in the pixel, it causes ionisation and the resulting charge is retained. When the pixel is enabled, that charge flows via the output and needs to be counted. Thus, the interpreter usually comprises an integrator, in which case the reset control is arranged to zero the integrator. Integrators are used to integrate the current into the photodiodes and thereby measure the charge that has passed.

The second approach to the problem lies in a reassessment of one of the assumptions behind the operating mode of the therapeutic accelerator. As mentioned above, this operates in a pulsed manner, with a duty cycle of approximately one in a thousand. Typically, this is a 3 μs pulse every 3 ms or thereabouts.

The total time required for a treatment will ideally be minimised. As time passes, the patient tires and may move or involuntary internal motion may occur, meaning that long treatment times can be less clinically effective. Further, a reduced treatment time can allow more patients to be treated, thereby increasing the clinical efficiency of the apparatus. Thus, from the desire to deliver the treatment in the minimum possible time, it can be inferred that there must be a very good reason indeed for the adoption of a duty cycle as low as 0.1%. Even a duty cycle as low as 1% would allow a tenfold improvement in clinical efficiency together with an (unqualified) improvement in clinical effectiveness.

That reason is the protection of the apparatus from thermal overload. The pulses that are delivered contain a high energy, and the energy required to produce them is also large. This energy must be dissipated, and (inevitably) some will appear as heat in the apparatus. The duty cycle needs to be low in order to prevent the temperature of the device becoming unacceptably high. The chosen duty cycle is that at which the rate of heat input to the device matches the rate of cooling that is provided.

We have realised that the existence of a time constant in the thermal behaviour of the device means that, in fact, it is the average duty cycle over the time constant that is important in this balance. If the duty cycle temporarily increases and then decreases, the apparatus may start to warm but will then cool before exceeding the limits of acceptable temperatures.

In a second aspect of the invention, therefore, we therefore provide a radiotherapeutic apparatus comprising a pulsed source of therapeutic radiation, a detector, and control circuitry for the pulsed source and the detector, the detector comprising an array of pixel elements, each having a signal output and an 'enable' input and being arranged to release a signal via the signal output upon being triggered by the enable input, the control circuitry being adapted prompt a plurality of pulses by the pulsed source and then enable a plurality of pixels of the array.

In effect, the therapeutic pulses are grouped into a "pulse of pulses"—a short flurry of pulses. During this time, the rate at which the apparatus is heated will exceed the rate at which it is being cooled, and the temperature can be expected to rise. However, it can be followed by longer period of downtime during which the apparatus will cool. During that downtime, the image can be collected from the imaging panel.

It is naturally preferred that the plurality of pixels comprises substantially all the pixels of the array. However, it is possible to collect part of the panel prior to delivering a further pulse of pulses. Generally, the arrays of pixels are two dimensional for ease of analysis. To speed the collection of images, the enable inputs of a group of pixels are connected in common thereby to enable the whole group simultaneously. If the pixels are grouped in rows within the 2D array, then that entire row can be read out at the same time. The outputs of each column of pixels can be passed to the interpreter or other output via a common output path.

Typical systems today have a maximum pulse rate of 400 to 600 pulses per second. The use of the above-described invention can allow this pulse rate to be increased to 1000 or even 1500 pulses per second during the periods while pulses are being produced.

The apparatus can include a separate source of diagnostic radiation, or the radiation for imaging purposes can be produced by a suitable therapeutic source, either by way of a portal image, or by controlling the source to produce lower energy radiation.

BRIEF DESCRIPTION OF THE DRAWINGS

An embodiment of the present invention will now be described by way of example, with reference to the accompanying figures, in which;

FIG. 1 shows the schematic structure of a flat panel imager;

FIG. 2 shows a detailed image of a small group of pixels in the flat panel imager;

DETAILED DESCRIPTION OF THE EMBODIMENTS

FIGS. 1 and 2 show an essentially standard imaging panel. FIG. 1 has been described already and shows the vertical cross-section through a single pixel. FIG. 2 shows sixteen pixels of the panel, a small portion of the entire panel but sufficient to explain the manner in which multiple pixels are read.

Referring to FIG. 2, therefore, the pixel array 26 is arranged in a rectilinear manner with the pixels in straight rows and columns. The intersection of a particular row 28 with a particular column 30 therefore defines a specific pixel 32. Each pixel has an associated transistor 34 to gate its output, and each row has a common "enable" line 36 which activates the transistor 34 of every pixel in that row.

Each column has a common output line 38 which allows the charge that has accumulated on each pixel to escape to an integrator 40 where it is multiplexed with the output of other columns. This allows the entire row to be read at the same time.

Figure 3:
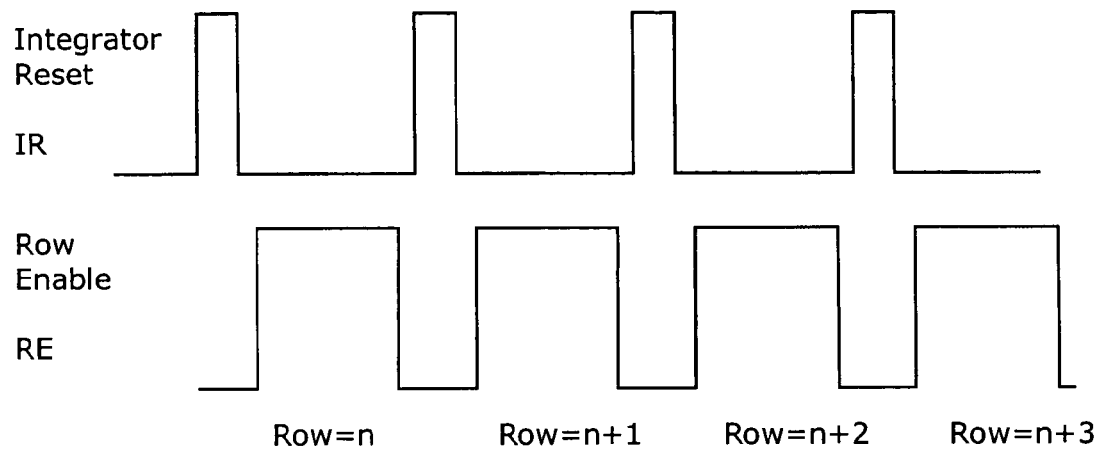
FIG. 3 shows a typical timing scheme for the flat panel imager of FIG. 2.

Scanning control electronics 42 therefore enables each row sequentially, and the whole row is read at substantially the same time. The integrator is then reset, and the next row is enabled. This timing scheme is shown in FIG. 3. A "row enable" signal RE is sent to each row in turn. After row 'n' has been enabled and the RE signal has finished, an "integrator reset" signal IR is sent to prepare the integrator for the signal from row 'n+1', and so on.

This does not however take account of the MV pulse that arrives from time to time. As noted above, that pulse causes ionisation in the row enable lines 36, the output lines 38, the transistors 34, and the integrator 40. All this adds to the charge collected by the integrator and will usually be sufficient to increase or perhaps saturate the signal, leading to a distinctive white line across an entire row.

Figure 4:
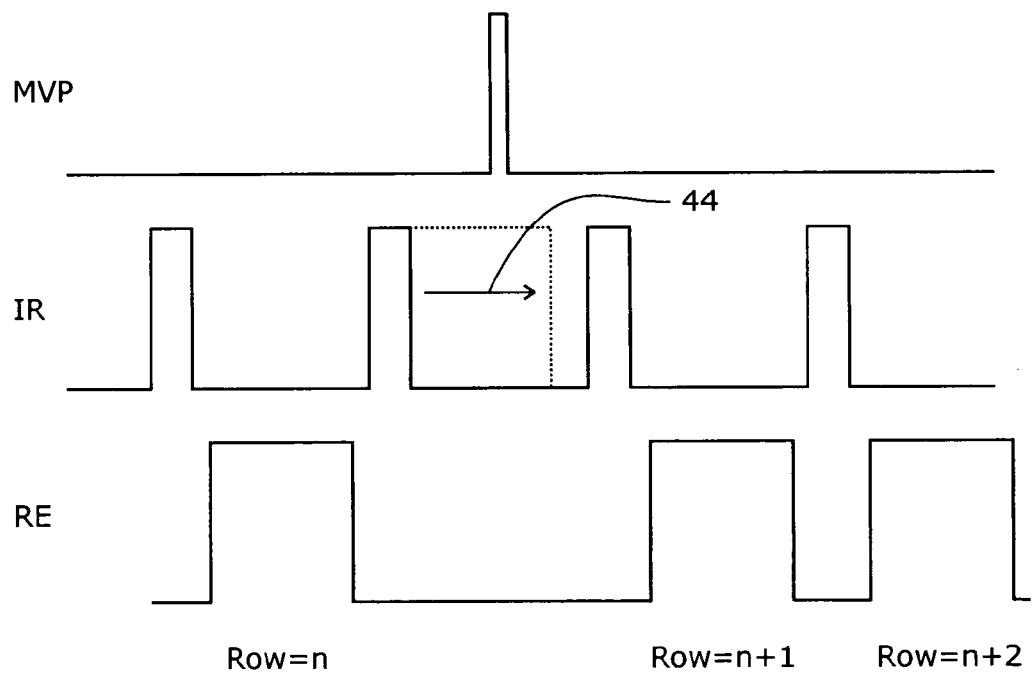
FIG. 4 shows a first revised timing scheme for such a flat panel imager.

FIG. 4 shows the revised timing schedule according to an embodiment of the invention. This figure shows the Megavoltage pulse (MVP) which takes place at a time dictated by the treatment control systems. The trigger signal for this pulse is also fed to the scanning control electronics, which prompts the previous IR signal to remain 'high' and for the RE signal to be suspended, until after the MVP has ceased. In effect, the IR signal is extended as shown at 44 until after the MVP ends, during which time the RE signal is suspended. The IR signal then ends, and the RE signals continue their cycle.

In this way, the aberrant signal delivered to the integrator by the MVP is substantially allowed to dissipate and the integrator is left zeroed after the MVP, ready to receive the signal from the next row. Most panels will in practice contain some parasite capacitance and resistance which prevents all the charge being removed from the panel, but this technique will substantially reduce the effect.

Figure 5:
FIG. 5 shows a typical timing scheme for a flat panel imager in the context of the arriving MV pulses.
Figure 5:
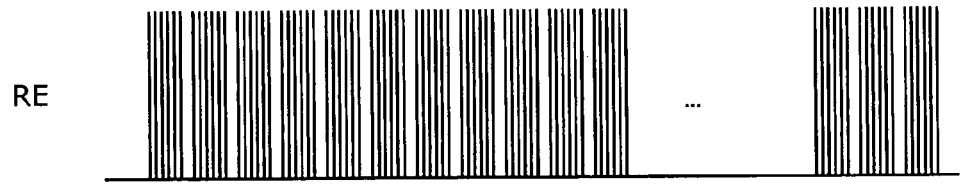
Figure 6:
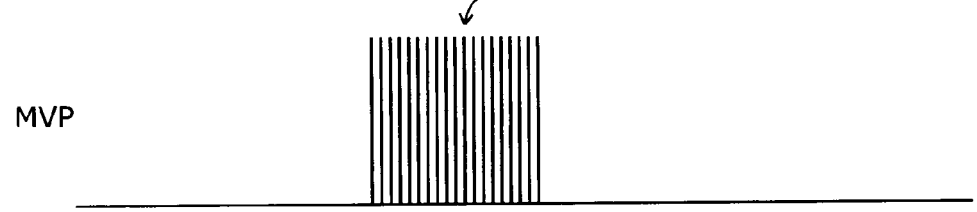
FIG. 6 shows a further revised timing scheme.
Figure 6:
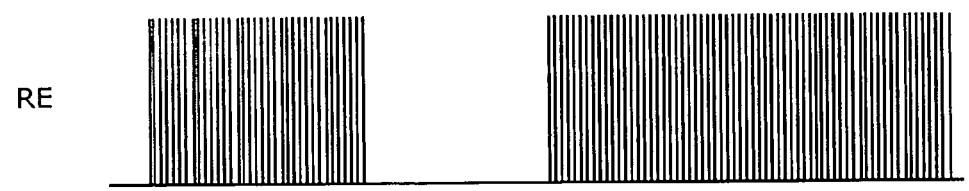

FIGS. 5 and 6 show the second embodiment of the invention. FIG. 5 shows the MVP and RE traces for a known system but on a much longer timebase than FIG. 3. Thus, several MVP triggers can be seen, along with several RE triggers between them. In general, between each MVP trigger the system has been able to read several rows of the panel.

FIG. 6 shows how this timing scheme is modified according to the present invention. The MVP triggers are grouped into a short flurry 46, with no RE triggers between them. After that flurry, the RE triggers resume and are continued until (in this case) the entire array has been read. After then, a new flurry of MVP triggers is delivered, and the panel is re-scanned by a fresh series of RE triggers.

Figure 7:
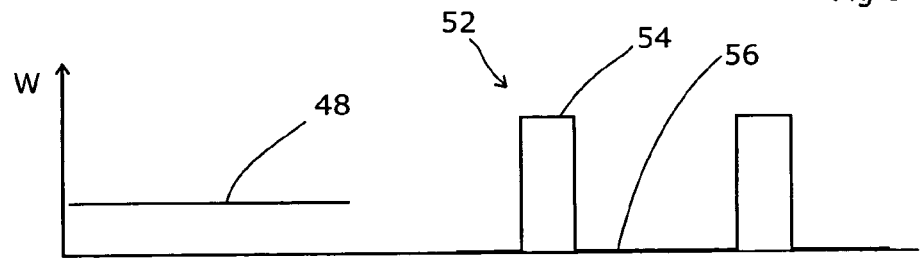
FIG. 7 shows the effect of the timing scheme of FIG. 6 on the thermal properties of the accelerator.
Figure 7:
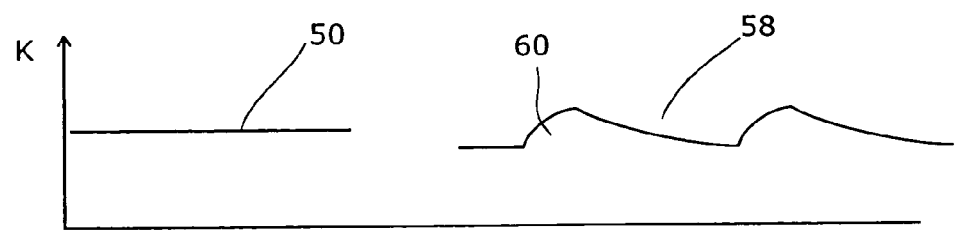

This means that, during the flurry 46 of MVP triggers, the rate of heat input into the device is temporarily higher. FIG. 7 shows a steady state of heat input 48 for a known system, which is the time-averaged heat input resulting from the MVP triggers of FIG. 5. This produces a steady temperature 50 which is the temperature at which the rate of heat input is balanced by the cooling systems provided. Adjacent the steady heat input 48 is shown the heat input 52 (over time) that is produced by the revised timing schedule of FIG. 6, in which there are regular peaks 54 during a flurry of MVP triggers 46, between which the rate of heat input falls to zero 56. This gives the temperature profile 58, a sawtooth with a rising edge 60 during the peaks 54 and a falling edge 58 between the flurries 46.

Clearly, if the higher rate of MVP triggers of a flurry 46 were to be maintained indefinitely, the apparatus would overheat. However, a critical temperature condition takes time to come into existence as the thermal mass of the device must be raised to the higher temperature by the application of sufficient heat energy. Therefore, there is time for a flurry 46; this moves the MVP triggers to create a gap during which the panel can be read. This means that either there are no MVP-induced artefacts in the image, or that the artefacts are confined to the first row that is read. In the latter case, that row can be arranged to be at an edge and therefore ignored.

Clearly, both embodiments could be combined, with the first embodiment being employed to prevent any artefacts appearing on even the first row of an image read according to the second embodiment. However, they are also susceptible to independent application.

It will of course be understood that many variations may be made to the above-described embodiment without departing from the scope of the present invention.

The invention claimed is:

1. A radiotherapeutic apparatus comprising a pulsed source of therapeutic radiation and a detector,
    the detector comprising control circuitry, an array of pixel elements, each pixel element having a signal output and an 'enable' input and being arranged to release a signal via the signal output upon being triggered by the enable input, and an interpreter arranged to receive the signal outputs of the pixel elements, the interpreter having a reset control;
    the control circuitry being adapted to reset the interpreter after a pulse of therapeutic radiation, prior to enabling at least one pixel element of the array.

2. The radiotherapeutic apparatus according to claim 1 in which the pixel elements output a signal in which the total charge passed reflects the total incident radiation since a predetermined instance.

3. The radiotherapeutic apparatus according to claim 2 in which the interpreter comprises an integrator.

4. The radiotherapeutic apparatus according to claim 3 in which the reset control is arranged to zero the integrator.

5. A radiotherapeutic apparatus comprising a pulsed source of therapeutic radiation, a detector and control circuitry for the pulsed source and the detector,
    the detector comprising an array of pixel elements, each having a signal output and an 'enable' input and being arranged to release a signal via the signal output upon being triggered by the enable input,
    the control circuitry being adapted to prompt a plurality of pulses by the pulsed source and then enable a plurality of pixel elements of the array.

6. The radiotherapeutic apparatus according to claim 5 in which the plurality of pixel elements comprises substantially all the pixels of the array.

7. The radiotherapeutic apparatus according to claim 5 in which the array is two dimensional.

8. The radiotherapeutic apparatus according to claim 7 in which the enable inputs of a group of pixel elements are connected in common thereby to enable the whole group simultaneously.

9. The radiotherapeutic apparatus according to claim 8 in which the pixel elements are grouped in rows within the 2D array.

10. The radiotherapeutic apparatus according to claim 8 in which the signal outputs of a plurality of pixel elements, each pixel element being of a different group, are passed to an interpreter via a common output path.

11. The radiotherapeutic apparatus according to claim 5 in which the pixel elements output a signal in which the total charge passed reflects the total incident radiation since a predetermined instance.

12. The radiotherapeutic apparatus according to claim 5 in which the pulse rate of the source is variable.

13. The radiotherapeutic apparatus according to claim 5 in which the pulse rate of the source is at least 1000 pulses per second.

14. The radiotherapeutic apparatus according to claim 5 in which the pulse rate of the source is at least 1500 pulses per second.

15. The radiotherapeutic apparatus according to claim 5 further comprising a separate source of diagnostic radiation.

16. The radiotherapeutic apparatus according to claim 6 in which the array is two dimensional.

17. The radiotherapeutic apparatus according to claim 5 in which the enable inputs of a group of pixel elements are connected in common thereby to enable the while group simultaneously.

18. The radiotherapeutic apparatus according to claim 6 in which the enable inputs of a group of pixel elements are connected in common thereby to enable the whole group simultaneously.

19. The radiotherapeutic apparatus according to claim 9 in which the signal outputs of a plurality of pixel elements, each being of a different group, are passed to an interpreter via a common output path.

20. The radiotherapeutic apparatus according to claim 7 in which the pixel elements output a signal in which the total charge passed reflects the total incident radiation since a predetermined instance.

* * * * *

UNITED STATES PATENT AND TRADEMARK OFFICE
CERTIFICATE OF CORRECTION

| | | |
|---|---|---|
| PATENT NO. | : 7,860,215 B2 | Page 1 of 1 |
| APPLICATION NO. | : 12/441005 | |
| DATED | : December 28, 2010 | |
| INVENTOR(S) | : Andrew Long et al. | |

It is certified that error appears in the above-identified patent and that said Letters Patent is hereby corrected as shown below:

Claim 17

Column 6, line 30, change "while" to "whole".

Signed and Sealed this
Fifth Day of April, 2011

David J. Kappos
*Director of the United States Patent and Trademark Office*